(12) United States Patent
Marissen (10) Patent No.: US 9,615,919 B2
(45) Date of Patent: Apr. 11, 2017

(54) IMPLANTABLE VALVE PROSTHESIS AND METHOD FOR MANUFACTURING SUCH A VALVE

(71) Applicant: Roelof Marissen, Born (NL)

(72) Inventor: Roelof Marissen, Born (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 14/634,603

(22) Filed: Feb. 27, 2015

(65) Prior Publication Data

US 2015/0238311 A1 Aug. 27, 2015

Related U.S. Application Data

(62) Division of application No. 13/059,469, filed as application No. PCT/EP2009/060729 on Aug. 19, 2009, now abandoned.

(30) Foreign Application Priority Data

Aug. 19, 2008 (EP) ..................................... 08014686

(51) Int. Cl.
*A61F 2/24* (2006.01)
*A61L 27/16* (2006.01)
*D04C 1/06* (2006.01)

(52) U.S. Cl.
CPC .............. *A61F 2/24* (2013.01); *A61F 2/2415* (2013.01); *A61L 27/16* (2013.01); *D04C 1/06* (2013.01); *A61F 2/2412* (2013.01); *A61F 2210/0014* (2013.01); *A61F 2240/002* (2013.01); *Y10T 29/49826* (2015.01)

(58) Field of Classification Search
CPC ................................................... A61F 2/2415

USPC ................................. 264/103, 320, 324, 325
See application file for complete search history.

(56) References Cited

U.S. PATENT DOCUMENTS

| 4,192,020 A | 3/1980 | Davis et al. |
| 5,445,883 A | 8/1995 | Kobayashi et al. |
| 5,549,666 A | 8/1996 | Hata et al. |
| 5,628,946 A * | 5/1997 | Ward ...................... A61L 27/14 |
| | | 156/296 |

(Continued)

FOREIGN PATENT DOCUMENTS

| CA | 1115002 | 12/1981 |
| CN | 201040049 Y | 3/2008 |

(Continued)

OTHER PUBLICATIONS

JP Office Action dated Jan. 6, 2015.

(Continued)

*Primary Examiner* — David Isabella
*Assistant Examiner* — Suba Ganesan
(74) *Attorney, Agent, or Firm* — Nixon & Vanderhye P.C.

(57) ABSTRACT

The invention relates to an implantable valve prosthesis, optionally comprising a support structure and at least one valve leaflet. The valve prosthesis comprises a material structure of unidirectional reinforcing elements of drawn ultra high molecular weight polyolefin, extending in at least two directions, wherein the modulus of elasticity of the polyolefin reinforcing elements is at least 60 GPa. The invention furthermore relates to a method for manufacturing such an implantable valve. The valve is easily manufactured and has an improved durability.

18 Claims, 4 Drawing Sheets

(56) References Cited

U.S. PATENT DOCUMENTS

| | | |
|---|---|---|
| 6,117,169 A | 9/2000 | Moe |
| 6,174,331 B1 | 1/2001 | Moe et al. |
| 6,454,798 B1 | 9/2002 | Moe |
| 6,475,239 B1 | 11/2002 | Campbell et al. |
| 6,482,343 B1 | 11/2002 | Cohen et al. |
| 6,558,418 B2 | 5/2003 | Carpentier et al. |
| 6,562,069 B2 | 5/2003 | Cai et al. |
| 6,613,086 B1 | 9/2003 | Moe et al. |
| 6,716,241 B2 | 4/2004 | Wilder et al. |
| 6,726,715 B2 | 4/2004 | Sutherland |
| 6,896,700 B2 | 5/2005 | Lu et al. |
| 6,936,067 B2 | 8/2005 | Buchanan |
| 7,988,900 B2 | 8/2011 | Beith |
| 2001/0021872 A1 | 9/2001 | Bailey et al. |
| 2003/0074059 A1 | 4/2003 | Nguyen et al. |
| 2003/0114913 A1 | 6/2003 | Spenser et al. |
| 2003/0114924 A1 | 6/2003 | Moe |
| 2003/0171802 A1* | 9/2003 | Wilder ............. A61F 2/2475 623/1.24 |
| 2003/0225447 A1 | 12/2003 | Majercak et al. |
| 2004/0254640 A1 | 12/2004 | Sutherland et al. |
| 2005/0137682 A1 | 6/2005 | Justino |
| 2005/0240262 A1 | 10/2005 | White |
| 2006/0085080 A1 | 4/2006 | Bechgaard et al. |
| 2006/0190074 A1* | 8/2006 | Hill ............. A61F 2/2412 623/1.23 |
| 2007/0135929 A1 | 6/2007 | Williams et al. |
| 2008/0075933 A1 | 3/2008 | Robers |
| 2008/0275540 A1 | 11/2008 | Wen |
| 2009/0112309 A1 | 4/2009 | Jaramillo et al. |
| 2010/0114307 A1 | 5/2010 | Agnew et al. |
| 2010/0185277 A1 | 7/2010 | Braido et al. |
| 2010/0249922 A1 | 9/2010 | Li et al. |

FOREIGN PATENT DOCUMENTS

| | | |
|---|---|---|
| EP | 1 574 811 | 9/2005 |
| FR | 2 980 968 | 4/2013 |
| JP | 1-310659 | 12/1989 |
| JP | 03-205151 | 9/1991 |
| JP | 2002-536115 | 10/2002 |
| JP | 2004-531355 | 10/2004 |
| JP | 2005-502429 | 1/2005 |
| WO | 00/47139 | 8/2000 |
| WO | 03/003943 | 1/2003 |
| WO | 03/024366 | 3/2003 |
| WO | 2004/032987 | 4/2004 |
| WO | 2006/000763 | 1/2006 |
| WO | 2006/002977 | 1/2006 |
| WO | 2007/028052 | 3/2007 |
| WO | 2007/122010 | 11/2007 |
| WO | 2007/123658 | 11/2007 |
| WO | 2010/054151 | 4/2010 |
| WO | 2012/094435 | 7/2012 |

OTHER PUBLICATIONS

International Search Report for PCT/EP2009/060729, mailed Nov. 10, 2009.

Written Opinion for PCT/EP2009/060729, mailed Nov. 10, 2009.

Japanese Office Action dated May 7, 2013.

* cited by examiner

IMPLANTABLE VALVE PROSTHESIS AND METHOD FOR MANUFACTURING SUCH A VALVE

CROSS-REFERENCE TO RELATED APPLICATIONS

This application is a divisional of U.S. application Ser. No. 13/059,469 filed 3 May 2011 (now abandoned), which is in turn the U.S. national phase of International Application No. PCT/EP2009/060729, filed 19 Aug. 2009, which designated the U.S. and claims priority to European Application No. 08014686.3, filed 19 Aug. 2008, the entire contents of each of which are hereby incorporated by reference.

FIELD

The invention relates to an implantable valve prosthesis and a method for manufacturing such an implantable valve prosthesis.

BACKGROUND AND SUMMARY

Implantable valve prostheses may for instance be used as a one-direction-valve prosthesis in the human or animal body, especially within or nearby blood vessels. A suitable valve prosthesis needs to open readily, cause no or only a little turbulence in the blood flow, and avoid regurgitation.

An aging population and increasing welfare lead to a higher demand for cardiovascular surgeries and their related products. Also, humans tend to demand more from their body since they live longer and perform increased physical exercise. Cardiovascular products, such as heart valve prostheses, are thus subject to increased requirements with respect to loading conditions, both in magnitude as in number of cycles. Typically, heart valve leaflets may undergo over a billion load cycles in their lifetime. Durability is therefore an important requirement.

An implantable valve prosthesis is described in NL1008349. The valve prosthesis of NL1008349 comprises a support structure carrying a number of valve leaflets. The valve leaflets are made by winding reinforcing fibers onto a mandrel in specific directions, as required by the occurring stresses in the leaflets. Since the fibers have to be positioned exactly according to the maximum stress lines, the known valve prosthesis is difficult to make and uses many wound layers to accommodate stresses, whereby mass is added. Moreover the known valve prosthesis can be improved further with respect to its durability, particularly in view of the increased requirements imposed on implantable valve prostheses nowadays.

Another implantable valve prosthesis is known from U.S. Pat. No. 6,726,715. As in NL1008349, the disclosed valve prosthesis comprises leaflets that are reinforced with fibers oriented along lines of stress in the leaflets. In this way, local variations of stress are accounted for. The valve prosthesis according to U.S. Pat. No. 6,726,715 suffers from the same disadvantage as the valve prosthesis of NL1008349, among others in that it is difficult to make.

WO 2004/032987 concerns a medical device having at least three layers of polymeric components arranged in a sandwich construction of which the polymeric component of the middle layer has a shorter chain length than the other polymeric components. A heart valve is mentioned as one possible application of the sandwich construction.

The object of the present invention is therefore to provide an implantable valve prosthesis that is readily manufactured and yet shows equal or improved durability over the prior art. Another object of the present invention is to provide a method for manufacturing such an improved valve prosthesis.

This object is achieved by providing an implantable valve prosthesis, comprising at least one valve leaflet and optionally a support structure for the at least one valve leaflet, the valve prosthesis being made of a material structure of unidirectional reinforcing elements of drawn ultra high molecular weight polyolefin, extending in at least two directions, wherein the modulus of elasticity of the polyolefin reinforcing elements is at least 60 GPa. By using the described 'two-directional' material structure, the valve prosthesis according to the invention is easily manufactured. Moreover it exhibits improved durability. This is surprising since it is well known that a high modulus of elasticity generally is associated with more brittle materials, thus yields unfavourable durability, in particular fatigue properties, due to the higher stress levels incurred.

BRIEF DESCRIPTION OF THE DRAWINGS

The invention will now be further elucidated by the following figures, without however being limited thereto.

DETAILED DESCRIPTION

By 'two-directional' is herein meant that the reinforcing elements are oriented in at least two directions for example at least two directions in a (curved) plane or surface or arranged in another three dimensional structure optionally in a matrix material, such as in two, three, four, five, six, seven, eight or even more directions.

The modulus of elasticity of the polyolefin is measured according to the standard ASTM D2256. The modulus measured, is the initial modulus as described in section 16 of ASTM D2256. Preferably the modulus of elasticity of the polyolefin reinforcement element is at least 65 GPa, More preferably at least 80 GPa. The maximum modulus is rather limited by the production technology of the polyolefin elements than by applicability in the valve prosthesis. So far, upper modulus limits for making superior valves are not encountered.

The valve prosthesis according to the invention comprises a material structure of unidirectional reinforcing elements extending in at least two directions. Such material structures may be produced while manufacturing the valve prosthesis or may, preferably, be produced beforehand as a semi-finished product. The valve prosthesis according to the invention is in particular advantageous since it allows using such relatively simple material structures, yet shows a good durability. Easy manufacturing is thus combined with long duration performance.

Since the valve prosthesis according to the invention preferably shows an increased fatigue strength over the prior art, thinner valve leaflets may be designed for similar fatigue strength in particular applications, such as in blood vessels. This saves additional mass.

In a first embodiment of the valve prosthesis according to the invention the thickness of the reinforcing elements is less than 40 micrometer, more preferably less than 30 micrometer and most preferably less than 20 micrometer. A valve prosthesis according to this preferred embodiment shows a combination of good deformability and fatigue resistance. Another advantage of the use of reinforcing elements with low thickness in the valve, and in particular in the valve leaflets, is that a high surface smoothness may be achieved, which benefits a low level of turbulence around the valve, and therefore diminishes the risk for blood coagulation.

In a preferred embodiment, the material structure comprises a plurality of superimposed multilayered material sheets, the sheets comprising a consolidated stack of monolayers of drawn ultra high molecular weight polyolefin, whereby the draw direction of two subsequent monolayers in the stack differs. It should be observed that this does not exclude the situation where some subsequent monolayers have the same draw direction as long as some of the (sets of) adjacent monolayers do have different draw direction. A stack of five layers where layer 3 and 4 have the same draw direction and this draw direction differs from layer 2 would hence be an embodiment of the invention (irrespective of the orientation of layer 1 and 5). However, in a preferred embodiment, most of the (sets of) subsequent monolayers have different draw direction, such as more than 50%, preferably more than 75% and most preferably more than 90%. With monolayers in the context of this application is meant layers comprising a plurality of unidirectional reinforcing elements of the drawn polyolefin, aligned in the same direction.

In another preferred embodiment the material structure comprises at least one material sheet, the at least one material sheet comprising a woven fabric of the drawn reinforcing elements. In yet another preferred embodiment, the material structure comprises a knitted braid of the drawn reinforcing elements. The fiber directions in a braid can be easily tuned by axial elongation and tend to readily accommodate the stresses in the leaflets, in particular in the leaflets of tricuspid valve prostheses. Furthermore, it was found that the handleability of braided and woven fabric is better than the handleability of unidirectional monolayers leading to a more flexible and affordable manufacturing processing.

In a highly preferred embodiment, the material structure consist of one woven fabric or knitted braid of the reinforcing elements of drawn ultra high molecular weight polyolefin. The woven fabric may for example be a 3D weaving or braiding forming a mechanically interlocked united structure having unidirectional reinforcing elements arranged in at least two directions. The material structure may also for example be wowen non-woven, knitted, braided or weaved structure (for example a number of UHMWPE UD tapes knitted together) or a material structure formed by any combination of these techniques, which creates a united structure. This is highly preferred, as it prevents or strongly reduced the risk of delaminating of a multilayered structure.

It is highly preferred that the structure does not comprise a sandwich structure with a soft material arranged between layers of UHMWPE, as it was found that this tend to lead to delamination of the valve construction due to failure of the soft layer or failure of the interface between the soft layer and one of the UHMWPE layers.

It is advantageous when the material structure comprises a plurality of drawn polyolefinic reinforcing elements embedded in a matrix binder. The binder may enclose the polyolefin reinforcing elements in their entirety or in part, such that the material structure is retained during handling and manufacturing of the valve leaflets. The binder may be applied in various forms or ways, for example as a film, that is melted to at least partially cover the polyolefin reinforcing elements, as a transverse bonding strip or as transverse reinforcing elements, or by impregnating and/or embedding the reinforcing elements with a polymer matrix in the form of a melt, a solution or a dispersion of a polymeric material in a liquid. In a preferred embodiment the binder is a polymeric matrix material, and may be a thermosetting material or a thermoplastic material, or a mixture of the two. If a thermosetting material is utilized, the thermosetting material is preferably at least partially cured and preferably fully cured in the final product. A matrix binder may also be added as a fibre with a lower melting point than the reinforcements in the fabric, hence allowing for melting and at least partially wetting of the UHMWPE during shaping of the valve. The elongation at break of the matrix material is preferably greater than the elongation of the polyolefin fibers. In case the matrix material is a thermosetting polymer, vinyl esters, unsaturated polyesters, epoxies or phenol resins are preferably selected. In case the matrix material is a thermoplastic polymer, polyurethanes, polyvinyls, polyacrylics, polyolefins and/or thermoplastic elastomeric block copolymers such as polyisoprene-polyethylene-butylene-polystyrene or polystyrene-polyisoprene-polystyrene block copolymers are preferably selected. Preferably, the amount of binder in the monolayers is at most 30% by weight, more preferably at most 25, 20 or even 15% by weight.

The reinforcing elements of the material structure may comprise fibres, unidirectional oriented tapes, bi-directional or multi directional oriented tapes, films or combinations of these. With unidirectional tapes or films is meant in the context of this application tapes or films, which show a preferred orientation of the polymer chains in one direction, i.e. in the direction of drawing. Such tapes and films may be produced by drawing, preferably by uniaxial drawing, and will in that case exhibit anisotropic mechanical properties.

The elements can be made with various technologies. Three technologies are presented in the following.

The first preferred technology is by melt processing of fibrous elements. A linear polyethylene with a number averaged molecular mass (Mn) between 30 000 and 700 000 should be preferably be chosen and a ratio between the weight averaged molecular mass (Mw) and Mn, should preferably not exceed a value of 2. So preferably Mw/Mn<2. in case Mn is in the lower range, a higher ratio can be accepted. However, for making strong elements, the upper range is preferred. Higher strength values are possible with high Mn values and low Mw/Mn ratios are then necessary in view of processing. Optimal conditions can be found by mere experimentation. After melting in an extruder, the material is fed through a set of orifices and a first elongation is achieved by drawing in the melt stage. Subsequent drawing of the fibers at increasing temperatures, but still below the melting point increases the tensile strength.

A second more preferred technology is by solid state processing of so-called disentangled polymers. An examples of such disentangled polymers is presented in WO93/1518 (incorporated herein by reference). An example of processing of such powders to strong members is presented in EP1627719 from p. 7 line 41 to p. 8, line 15 (incorporated herein by reference). A difference between EP1627719 and the present members is that the members in EP1627719 are for ballistic purposes. The width for the present application would be chosen to be much smaller. However, essential changes in the process are not necessary.

A third and the most preferred technology is so-called gel spinning. Many publications are available on this. An example is WO2005/066401 (incorporated herein by reference).

Drawing, preferably uniaxial drawing, of the produced films may be carried out by means known in the art. Such means comprise extrusion stretching and tensile stretching on suitable drawing units. The stretching may also be biaxial or multi axial—particularly when the stretched member is not unidirectional. To attain increased mechanical strength and stiffness, drawing may be carried out in multiple steps.

The strength of the reinforcing elements in the material structure depends amongst others on the polyolefin from which they are produced, the production method of the fiber and on their (uniaxial) stretch ratio. The tensile strength of the reinforcing elements measured in the direction of the fiber is preferably at least 0.9 GPa, more preferably at least 1.2 GPa, even more preferably at least 1.5 GPa, even more preferably at least 1.8 GPa, even more preferably at least 2.1 GPa, and most preferably at least 3 GPa. The strength of the material structure will generally depend on the volume fraction of the reinforcing elements in the material structure.

In yet another preferred embodiment the valve prosthesis according to the invention is substantially free of matrix binder. Such an embodiment is more effective, having the same mechanical performance for less material. Moreover this embodiment improves blood compatibility. If no matrix binder is used, the polyolefin fibers may preferably be partially fused during the manufacturing of the final product.

The fibres, unidirectional oriented tapes and films preferably comprise ultra high molecular weight polyethylene. The ultra high molecular weight polyethylene may be linear or branched, although preferably linear polyethylene is used. Linear polyethylene is herein understood to mean polyethylene with less than 1 side chain per 100 carbon atoms, and preferably with less than 1 side chain per 300 carbon atoms; a side chain or branch generally containing at least 10 carbon atoms. Side chains may suitably be measured by FTIR on a 2 mm thick compression moulded film, as mentioned in e.g. EP 0269151. The linear polyethylene may further contain up to 5 mol % of one or more other alkenes that are copolymerisable therewith, such as propene, butene, pentene, 4-methylpentene, octene. Preferably, the linear polyethylene is of high molar mass with an intrinsic viscosity (IV, as determined on solutions in decalin at 135° C.) of at least 4 dl/g; more preferably of at least 8 dl/g, most preferably of at least 10 dl/g. Such polyethylene is also referred to as ultra high molecular weight polyethylene, UHMWPE. In case of the preferred ultra high molecular weight polyethylene films, drawing is typically carried out uniaxially in a number of drawing steps. The first drawing step may for instance comprise drawing to a stretch factor of 3. Multiple drawing may typically result in a stretch factor of 9 for drawing temperatures up to 120° C., a stretch factor of 25 for drawing temperatures up to 140° C., and a stretch factor of 50 for drawing temperatures up to and above 150° C. By multiple drawing at increasing temperatures, stretch factors of about 50 and more may be reached. This results in high strength tapes, whereby for tapes of ultra high molecular weight polyethylene, strengths more than 3 GPa may be obtained.

The thickness of the material structure, and in particular of the material structure in the valve leaflets, may be varied within large ranges. However, preferably the thickness of the material structure ranges between 50 and 500 micrometer, more preferably between 80 and 400 micrometer and most preferably between 150 and 250 micrometer. Such thickness allows for effective closing and opening of the valve leaflets with minimal effort and minimal regurgitation (blood flow in a non desired direction), while maintaining sufficient durability.

In a preferred embodiment at least one valve leaflet is integrally formed with at least a part of the support structure. Using a material structure in the form of a semi-finished product comprising reinforcing elements extending in at least two directions allows to readily integrate structures with different design requirements. Integrating support structure and leaflets establishes a durable connection between the two.

In another preferred embodiment the support structure (also referred to as stent) of the valve prosthesis according to the invention comprises a rigid member, and more preferably is ring shaped. Suitable materials for making the support structure include rigid polymers, fibre reinforced polymers, metals and their alloys, ceramics and combinations thereof.

Suitable rigid polymers include polyacetals such as Delrin® and Celcon®, dextroplast, polyurethane, polyethylene, rubber, polysulfones, polyethersulfones, polyarylsulfones, polyetheretherketones, and polyetherimides. Suitable metals include biocompatible metals, such as, stainless steel, titanium, cobalt alloys, such as Elgiloy®, a cobalt-chromium-nickel alloy, and MP35N, a nickel-cobalt-chromium-molybdenum alloy, and Nitinol®, a nickel-titanium alloy. In addition, stents can be produced from ceramic materials, such as pyrolytic carbon, silicon carbides or metal carbides, hydroxyapatite and alumina. Suitable stents can also be produced from carbons such as graphite.

Preferably, the support structure is at least partly made from a super elastic alloy, or a shape memory alloy, such as Nitinol®, a nickel-titanium alloy, that is available as a super elastic material, as well as a shape memory alloy. Such a support structure allows to easily insert the valve prosthesis into the body in a desired position. Before insertion, the support structure is brought to a first (relatively low) temperature at which is has a compact configuration. This compact configuration allows to easily insert the support structure (and the leaflets) into the body, using minimal invasive surgery. After positioning the support structure, and due to the body temperature, the shape memory alloy will heat up and change phase, thereby changing its shape. For Nitinol® for instance, a phase change will occur between an austenitic phase and a martensitic phase. As a result the support structure will expand and thereby creates a clamping force against surrounding tissue. In another configuration, Nitinol® is super elastic and can be deformed up to material strains of about 10%, thus deformation of a valve towards a compact shape is possible, still allowing elastic deployment to the final shape after placement.

The invention also relates to a process for the manufacture of an implantable valve prosthesis, the process comprising the steps of:

(a) providing a material structure of unidirectional reinforcing elements of drawn ultra high molecular weight polyolefin, extending in at least two directions, wherein the modulus of elasticity of the polyolefin reinforcing elements is at least 60 GPa;
(b) shaping the material structure in the form of at least a part of the valve prosthesis;
(c) consolidating the material structure under elevated temperature and pressure.

Preferably, the process steps are applied in the given order, as this allows for accurate individual production of the valve prostheses. However this is not necessary and process steps may be reversed. For instance, it is also possible to first consolidate the material structure and thereafter shape at least part of the valve prosthesis by for instance taking away surplus material.

Consolidation may suitably be done in a hydraulic press. Consolidation is intended to mean that (at least part of) the material structure is relatively firmly cohered to form one unit. The temperature during consolidating generally is controlled through the temperature of the press. A minimum temperature generally is chosen such that a reasonable speed of consolidation is obtained. In this respect 80° C. is a suitable lower temperature limit, preferably this lower limit is at least 100° C., more preferably at least 120° C., most preferably at least 140° C. A maximum temperature is chosen below the temperature at which the drawn polyolefin reinforcing elements lose their high mechanical properties due to e.g. melting. Preferably the temperature is at least 5° C., preferably at least 10° C. and even more preferably at least 15° C. below the melting temperature of the drawn polyolefin reinforcing elements. In case the drawn polyolefin reinforcing elements do not exhibit a clear melting temperature, the temperature at which the drawn polyolefin reinforcing elements starts to lose their mechanical properties should be read instead of melting temperature. In the case of the preferred ultra high molecular weight polyethylene, a temperature below 149° C., preferably below 145° C. generally will be chosen. The pressure during consolidating preferably is at least 7 MPa, more preferably at least 15 MPa, even more preferably at least 20 MPa and most preferably at least 35 MPa. The optimum time for consolidation generally ranges from 5 to 120 minutes, depending on conditions such as temperature, pressure and thickness and can be verified through routine experimentation.

Preferably, cooling after compression moulding at high temperature is carried out under pressure as well. Pressure is preferably maintained at least until the temperature is sufficiently low to prevent relaxation. This temperature can be established by one skilled in the art.

In another preferred embodiment of the process according to the invention, a polymer is applied onto the material structure, more preferably preceding consolidation of the material structure. The advantage of applying a polymer onto the materials structure before consolidation is that it will at least partly impregnate the reinforcing elements, which leads to improved coherence of the material structure and thereby to improved durability.

Figure 1:
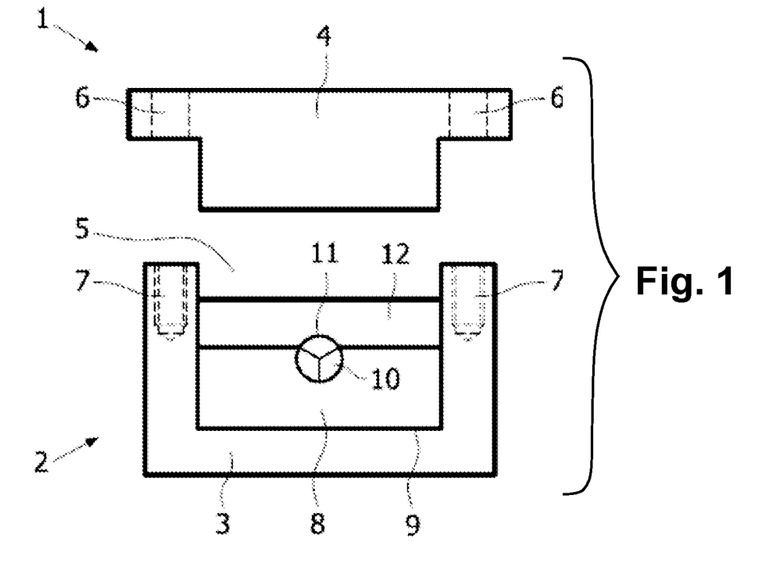
FIG. 1 schematically represents a cross section of an apparatus for making a valve prosthesis according to the invention, with the apparatus in opened configuration.

Referring to FIG. 1, an example of an apparatus 1 for manufacturing a valve prosthesis according to the invention is shown. The apparatus 1 comprises a box like holder 2, provided with a closure 4. Within holder 2, an inner mould 10, made of hard steel, and defining the inner shape of the valve to be produced, is provided. Around inner mould 10, a rubber mould (8, 12) is provided. Holder 2 and closure 4 enclose rubber mould (8, 12) to pressurize it. Holder 2 comprises steel walls 3, provided with integrated heating elements (not shown). Closure 4 is also made of steel and provided with integrated heating elements (not shown). Closure 4 is dimensioned such that it partly fits into the inner space 5 of holder 2. Bolt holes 6 are provided in closure 4 to match the inner screw thread 7 of the steel walls 3 of holder 2, and attach closure 4 to holder 2. Lower rubber mould halve 8 is positioned on the bottom 9 of the inner space 5 of holder 2. An upper mould halve 12 is positioned over lower mould halve 8. Both rubber mould halves (8, 12) enclose hard mould 10, which is provided with a hollow braid 11 as material structure.

Figure 2:
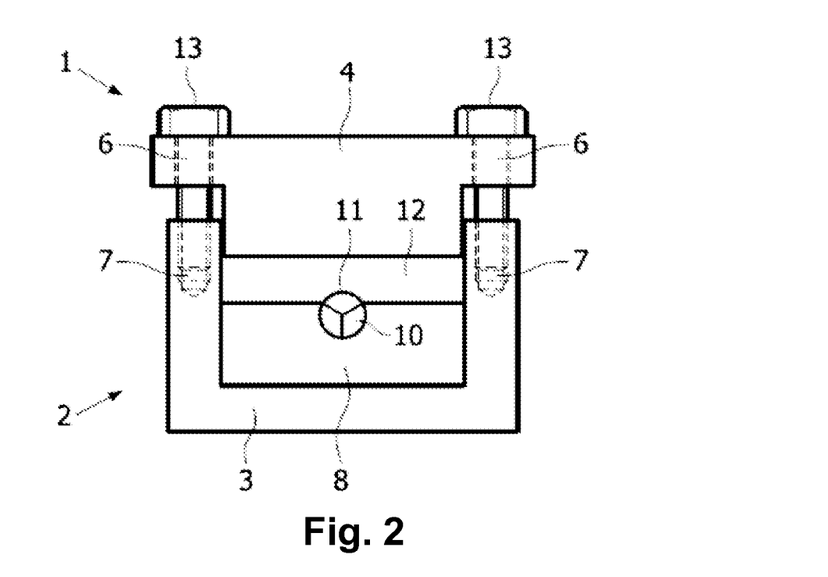
FIG. 2 schematically represents a cross section of an apparatus for making a valve prosthesis according to the invention, with the apparatus in closed configuration.

Referring now to FIG. 2, the rubber moulds (8, 12) are pressurized by lowering closure 4 into inner space 5 of holder 2, until it contacts the upper mould halve 12. Bolts 13 are placed through bolt holes 6 of closure 4 and partly positioned into the screw thread 7 of the steel walls 3 of holder 2.

Figure 3:
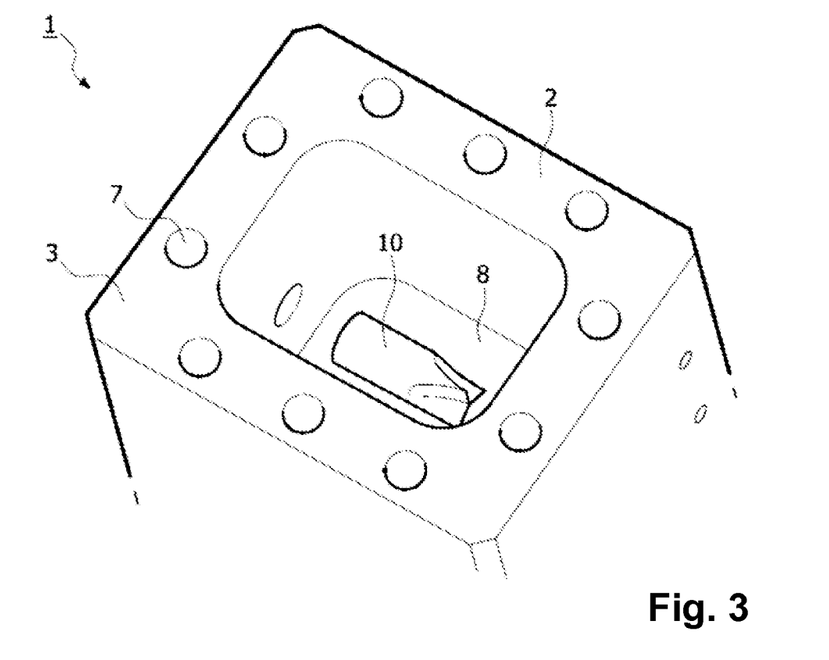
FIG. 3 schematically represents a detailed view in perspective of the apparatus of FIG. 1.

In a preferred embodiment, lower and upper mould halves (8, 12) are manufactured as follows. Holder 2 is filled about half way (see FIGS. 2 and 3) with a two component curable silicone rubber resin Silastic® MRTV silicone rubber from Dow Corning. Hard mould 10 is then placed half way in the still uncured rubber of the lower mould halve 8 by suspending it from a thermocouple (not shown), connected to the walls 3 of the holder 2. The hard mould 10 was treated with a release agent. After curing the lower mould halve 8, the hard mould 10 is removed from lower mould halve 8 and replaced again. Another layer of release agent is then applied. Subsequently, an additional portion of rubber mixture is applied on top of lower mould have 8 with the hard mould 10 positioned onto the lower mould halve 8 to form the upper mould halve 12. Sufficient rubber is applied to ensure that closure 4, when inserted into the inner space 5 of holder 2, exerts enough pressure onto the lower and upper mould halves (8, 12). After curing the upper mould halve 12, the lower and upper mould halves (8, 12), as well as the hard mould 10 are taken apart and all rests of release agent removed. If desired, the rubber cavities in the lower and upper mould halves (8, 12), as formed by the hard mould 10, can be extended by cutting away some material, for instance with a knife.

Various valve designs are known in the art. In the following sections one preferred embodiment is described in details, however, based on this the skilled person would be able to adjust known manufacturing methods to that of the present invention.

Figure 4:
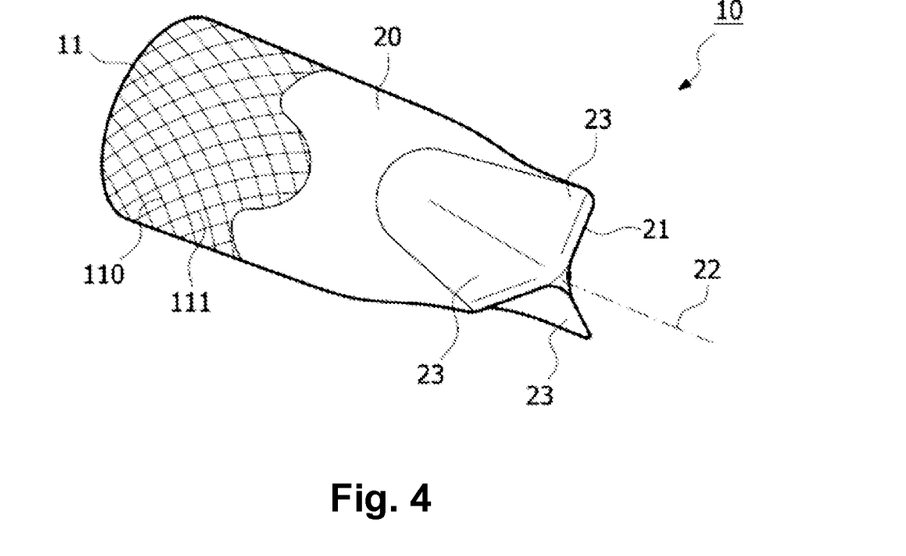
FIG. 4 schematically represents a hard mould, representing the inner volume of a heart valve prosthesis according to the invention, the hard mould being shown partially covered by reinforcing elements.

In one way of producing a valve according to the invention, the lower mould halve 8 is placed onto the bottom 9 of the holder 2. A hollow braid 11 with a diameter of 2 centimeter and strands (110, 111) oriented at ±45° angle with the longitudinal axis, which strands are made from commercial Dyneema® SK75 fibers is pulled over the hard mould 10, as shown in FIG. 4. Reinforcing elements in the form of strands (110, 111) extend in two directions. A first series 110 of strands extends at an angle of about 90° with respect to a second series of strands 111. The inner mould 10 defines the inner shape of the valve to be produced. In FIG. 4, the hard mould 10 is covered by a partially shown braid 11. The hard mould comprises a tubular part 20 and a star-shaped part 21 with a longitudinal central axis 22. The star shaped part 21 comprises three surfaces 23, which are curved towards the longitudinal central axis 22. The three surfaces 23 of the mould 10 form the support for the leaflets of the valve prosthesis during manufacturing thereof. The tubular part 20 of the hard mould 10 extends beyond the dimensions of the valve prosthesis in its final form, to allow for easy positioning of the braid 11. About 2 mm excess material at both sides of the mould 10 is left. A Mylar (polyethylene terephthalate) film (not shown) is then placed over the braid 11. The assembly of hard mould 10, covered by the braid 11, and the Mylar film is then placed in the mould cavity of the lower mould halve 8. Subsequently, the upper mould halve 12 and the closure 4 are placed on top, such that closure 4 makes contact with the upper mould halve 12. Bolts 13 are applied and tightened such that an estimated pressure exceeding 30 MPa is applied on the mould halves (8,12). After tightening the bolts 13, the heating system is switched on. The heating system is controlled such that a temperature of 145° C. occurs in the hard mould 10. The temperature in the hard mould 10 is measured with a thermocouple. Heating is switched off when the hard mould 10 is subjected to a temperature of 145° C. during one hour. The complete apparatus including the valve is allowed to cool down during a day and was then opened. The front and back sides of the moulded valve prosthesis is then edge trimmed carefully, removing any excess material. Edge trimming is done with the hard mould 10 still inside, using a very sharp razor blade, making sawing movements. Sharpness and sawing movements are necessary in view of the cut resistance of the Dyneema® SK75 fibers. Finally, the valve prosthesis is demoulded by pulling it away from the hard mould 10. During the above described moulding process, the individual Dyneema® fibers were fused together in the shape of a valve prosthesis.

In a preferred embodiment, the shaping of the material structure in the mould is conducted mainly or (preferably) solely by creep forming. This reduces the risk of formation of ripple in the structure and hence provides a more uniform structure and smooth surface than traditional forming processes where ripples may be formed.

Another embodiment of the invented valve was made, using a similar procedure as described above, the difference being that a low density polyethylene film with a thickness of 10 micrometer was applied around the braid 11, before covering it with a Mylar® film. Temperature was set at 135° C., being sufficient to melt the low density polyethylene film, thereby impregnating the fibers of the braid 11.

Figure 6:
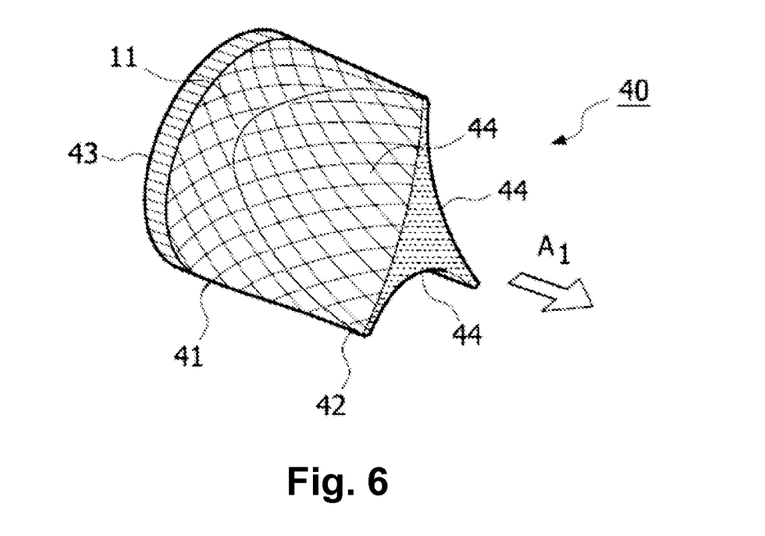
FIG. 6 schematically represents a heart valve prosthesis according to the invention with the leaflets in an almost opened position.

After demoulding, any excess material of the tubular part 20 is removed, and a support structure attached thereto. Referring to FIG. 6, the valve prosthesis 40 comprises a ring-shaped support structure 43, made from Nitinol®, which is a commercially available nickel-titanium alloy. The valve prosthesis 40 furthermore comprises three leaflets 44, which are an integrated part nearby the support structure 43, as they are shaped from the braid 11. The braid 11 is fixed to the support structure 43 by sutures (not shown).

Figure 5:
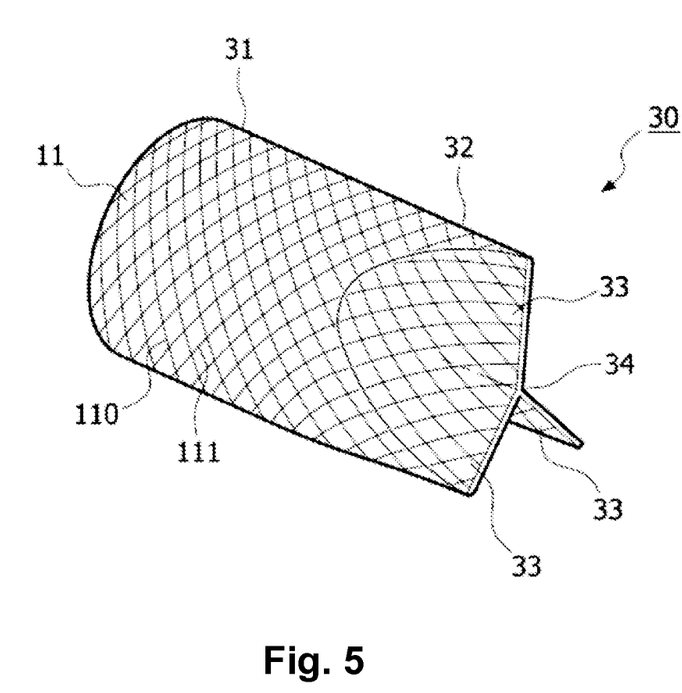
FIG. 5 schematically represents a semi-finished heart valve prosthesis according to the invention, manufactured using the apparatus of FIG. 1 and the hard mould of FIG. 4.

A semi-finished heart valve prosthesis 30 according to the invention and manufactured using the device 1 of FIGS. 1 and 2 as well as the hard mould 10 of FIG. 4 is shown in FIG. 5. The semi-finished heart valve prosthesis 30 comprises a tubular part 31 and a star shaped part 32, which are integrally formed by the braid 11 with strands (110, 111). The star shaped part 32 comprises three surfaces 33, which are curved towards the longitudinal central axis 34, which surfaces 33 form the leaflets of the semi-finished heart valve prosthesis 30. The semi-finished heart valve prosthesis 30 may need further processing steps, such as shortening of the tubular part 31 as well as adding a support structure.

Figure 7:
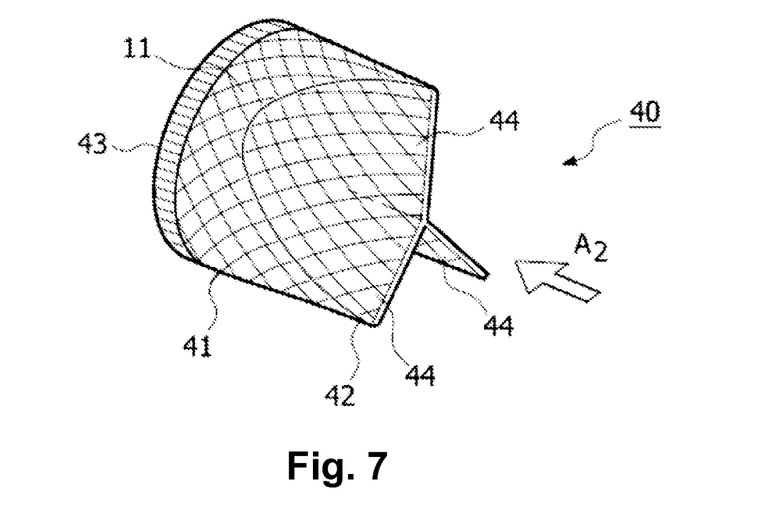
FIG. 7 schematically represents a heart valve prosthesis according to the invention with the leaflets in a closed position.

FIGS. 6 and 7 show a heart valve prosthesis 40 according to the invention, manufactured from the semi-finished prosthesis of FIG. 5. The heart valve prosthesis 40 is obtained by shortening the tubular part 31 of the semi-finished heart valve prosthesis 30, for example by using a hot knife, and by fixing a support structure 43 to the shortened end of the tubular part 41. The valve prosthesis 40 comprises a ring-shaped support structure 43, for example made from Nitinol®, which is a commercially available nickel-titanium alloy. The valve prosthesis 40 furthermore comprises three leaflets 44, which are integrally part of the valve connected to themselves nearby the support structure 43, as they are shaped from the braid 11. The braid 11 is fixed to the support structure 31 by sutures (not shown). It is obvious to the skilled person that other numbers of leaflets 44, such as 1, 2, 4, 5, 6 or even more, may also be used (not shown in the figures).

In fact this valve prosthesis 40 is a tube with collapsed walls in a tricuspid shape, forming the star shaped part 42. The leaflets 44 easily open with a light pressure towards the end. However, pressure in the other direction will cause additional closing pressure, thus preventing regurgitation.

In FIG. 6, the leaflets 44 are depicted in open position, as medium flows in the direction according to the arrow A1.

FIG. 7 shows the valve prosthesis 30 of FIG. 6, but now with the leaflets 44 in a closed position. This is the result of medium flowing in the direction according to the arrow A2 towards the valve prosthesis 40. As the leaflets 44 of FIG. 6 are configured such that they slightly extend from the support structure towards a central longitudinal axis 34 of the semi-finished heart valve prosthesis 30 of FIG. 5, a small pressure difference as a result of medium flowing in the direction according to arrow A2, will press the leaflets 44 towards each other, thereby closing the valve prosthesis 40 and preventing the medium to flow through the valve prosthesis 40 according to arrow A2.

To aid in avoiding regurgitation, the valves are preferably produced in a shape that conforms to the closed position, because a slight pressure in the desired flow direction will cause opening of this embodiment, while the closed position will be approached rapidly if the pressure is reversed.

The invention claimed is:

1. A method of manufacturing an implantable valve prosthesis comprising at least one valve leaflet and a support structure, comprising the steps of:
    (a) providing a material structure consisting of one woven, non-woven, knitted or braided fabric of unidirectional reinforcing elements of drawn ultra high molecular weight polyethylene extending in at least two directions, wherein the modulus of elasticity of the reinforcing elements is at least 60 GPa, and wherein the material structure is substantially free of matrix binder;
    (b) shaping the material structure into a form of at least a part of the valve prosthesis using a mold defining an inner shape of the valve;
    (c) consolidating the material structure under elevated temperature and pressure, wherein the temperature is at least 80° C. and below the temperature at which the reinforcing elements lose their high mechanical properties due to melting; and
    (d) fixing the support structure to the material structure to integrate at least a part of the support structure and the least one valve leaflet.

2. The method according to claim 1, wherein the material structure is a hollow braid.

3. The method according to claim 1, wherein the reinforcing elements are fibers.

4. The method according to claim 1, wherein the reinforcing elements have a thickness of less than 40 micrometer.

5. The method according to claim 1, wherein the material structure has a thickness of between 50 and 500 micrometer.

6. The method according to claim 1, wherein shaping the material structure is conducted by creep forming.

7. The method according to claim 1, wherein the valve prosthesis has three valve leaflets.

8. The method according to claim 1, wherein the at least one valve leaflet is made in a shape that conforms to a closed position of the valve prosthesis.

9. The method according to claim 1, wherein the temperature during consolidating is at least 100° C. and below 149° C.

10. The method according to claim 1, wherein the temperature during consolidating is at least 120° C. and below 145° C.

11. The method according to claim 1, wherein the pressure during consolidating is at least 15 MPa.

12. The method according to claim 1, wherein the pressure during consolidating is at least 20 MPa.

13. The method according to claim 1, further comprising cooling under pressure after shaping and consolidating.

14. The method according to claim 1, wherein the support structure is ring-shaped.

15. The method according to claim 1, wherein the support structure is made from rigid polymers, fiber reinforced polymers, metals and their alloys, ceramics, or combinations thereof.

16. The method according to claim 1, wherein the support structure is at least partly made from a super elastic alloy or a shape memory alloy.

17. The method according to claim 1, wherein the implantable valve prosthesis is a heart valve prosthesis.

18. An implantable valve prosthesis made by the method according to claim 1.

* * * * *